US012642655B2

(12) United States Patent
Zhang et al.

(10) Patent No.: US 12,642,655 B2
(45) Date of Patent: Jun. 2, 2026

(54) VALVE CLAMPING DEVICE WITH ADJUSTABLE BEARING FORCE AND VALVE CLAMPING SYSTEM

(71) Applicant: HANGZHOU VALGEN MEDTECH CO., LTD., Hangzhou (CN)

(72) Inventors: Tingchao Zhang, Hangzhou (CN); Weiwei Zhang, Hangzhou (CN); Xianzhang Zheng, Hangzhou (CN); Huaguang Liang, Hangzhou (CN)

(73) Assignee: Hangzhou Valgen Medtech Co., Ltd., Hangzhou (CN)

( * ) Notice: Subject to any disclaimer, the term of this patent is extended or adjusted under 35 U.S.C. 154(b) by 614 days.

(21) Appl. No.: 18/042,022

(22) PCT Filed: Aug. 17, 2021

(86) PCT No.: PCT/CN2021/112918
§ 371 (c)(1),
(2) Date: Feb. 17, 2023

(87) PCT Pub. No.: WO2022/037559
PCT Pub. Date: Feb. 24, 2022

(65) Prior Publication Data
US 2024/0008983 A1      Jan. 11, 2024

(30) Foreign Application Priority Data

Aug. 17, 2020    (CN) ......................... 202010827144.X
Aug. 17, 2020    (CN) ......................... 202021717911.3

(51) Int. Cl.
*A61F 2/24*         (2006.01)

(52) U.S. Cl.
CPC ............ *A61F 2/246* (2013.01); *A61F 2/2466* (2013.01); *A61F 2210/0014* (2013.01); *A61F 2220/0008* (2013.01)

(58) Field of Classification Search
CPC .................... A61F 2/246; A61F 2/2466; A61F 2210/0014; A61F 2220/0008
See application file for complete search history.

(56) References Cited

U.S. PATENT DOCUMENTS 10,076,415 B1 *   9/2018   Metchik .................. A61F 2/246
10,959,847 B2 *   3/2021   Metchik .................. A61F 2/246
(Continued)

FOREIGN PATENT DOCUMENTS

CN         106491245 A       3/2017

*Primary Examiner* — Suzette J Gherbi
(74) *Attorney, Agent, or Firm* — Sand, Sebolt & Wernow Co., LPA

(57) ABSTRACT

Disclosed are a valve clamping device with an adjustable bearing force and a valve clamping system. The valve clamping device with an adjustable bearing force comprises: a support portion comprising a connecting end and a free end disposed oppositely; a hollow adjustment portion made of a shape memory material, one end of which is sleeved outside the connecting end and connected to the support portion, and another end of which hangs in air; a clamping portion enclosed outside the adjustment portion; and a driving portion connected to the clamping portion to drive the clamping portion to open or close around the adjustment portion; wherein the free end of the support portion is within the adjustment portion, and a proximal end of the adjustment portion is spaced apart from a proximal end of the support portion.

17 Claims, 13 Drawing Sheets

(56) References Cited

U.S. PATENT DOCUMENTS

| | | | |
|---|---|---|---|
| 2017/0239048 A1* | 8/2017 | Goldfarb | A61F 2/2442 |
| 2020/0030098 A1 | 1/2020 | Delgado et al. | |
| 2020/0113695 A1* | 4/2020 | McCann | A61B 17/00234 |
| 2023/0338145 A1* | 10/2023 | Oberwise | A61F 2/2463 |
| 2024/0122709 A1* | 4/2024 | Freschauf | A61F 2/246 |
| 2025/0241757 A1* | 7/2025 | Bloodworth, IV | A61F 2/246 |

* cited by examiner 520
522
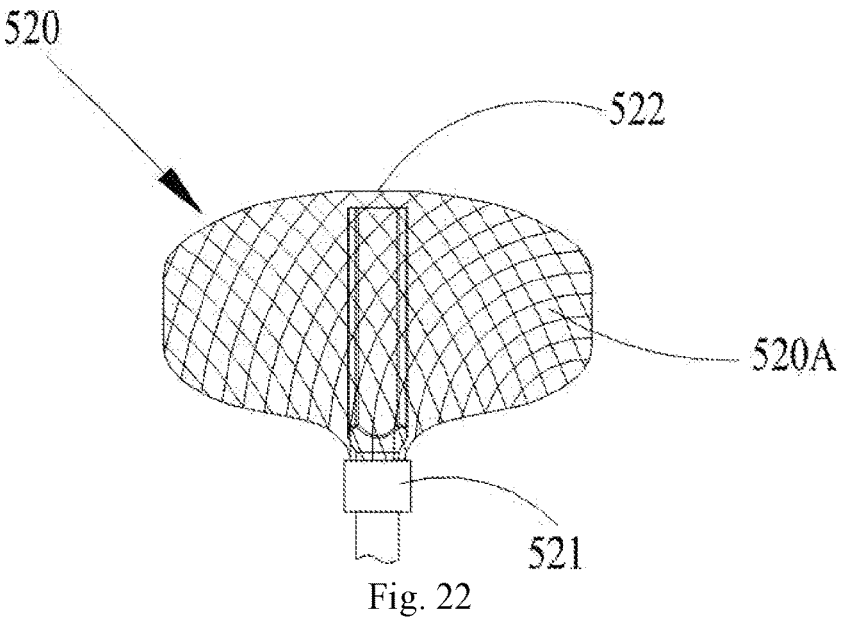
520A
521
Fig. 22
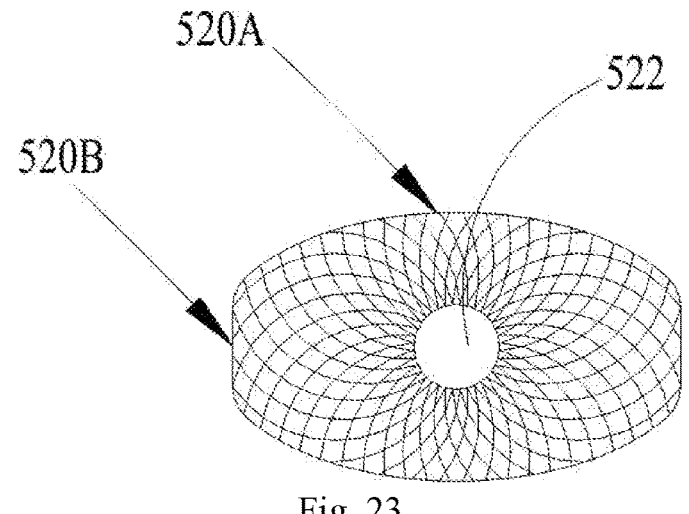
520A
522
520B
Fig. 23
512
522
510
521b
511
520B
521a
Fig. 24

VALVE CLAMPING DEVICE WITH ADJUSTABLE BEARING FORCE AND VALVE CLAMPING SYSTEM

CROSS-REFERENCE TO RELATED APPLICATIONS

The present disclosure claims all the benefits of the Chinese patent application No. 202010827144.X, filed on Aug. 17, 2020 before the China National Intellectual Property Administration of the People's Republic of China, entitled "Valve Clamping Device with Adjustable Bearing Force and Valve Clamping System", and the Chinese utility model application No. 202021717911.3, filed on Aug. 17, 2020 before the China National Intellectual Property Administration of the People's Republic of China, entitled "Valve Clamping Device with Adjustable Bearing Force and Valve Clamping System", which are explicitly incorporated herein by reference in their entirety.

FIELD

The present disclosure relates to a field of implanted medical devices, particularly to a valve clamping device with an adjustable bearing force and a valve clamping system.

BACKGROUND

Referring to FIG. 1, a mitral valve 1 is a one-way valve located between a left atrium 2 and a left ventricle 3 of the heart, a normal and healthy mitral valve 1 can control blood to flow from the left atrium 2 to the left ventricle 3 while avoiding blood from flowing from the left ventricle 3 to the left atrium 2. The mitral valve 1 comprises a pair of valve leaflets, called an anterior leaflet 1a and a posterior leaflet 1b. The anterior leaflet 1a and posterior leaflet 1b are fixed to papillary muscles of the left ventricle 3 by chordae tendineae 4. Normally, when the left ventricle 3 of the heart contracts, edges of the anterior leaflet 1a and the posterior leaflet 1b are fully conjoined to avoid blood from flowing from the left ventricle 3 to the left atrium 2. Referring to FIG. 2, when the valve leaflet of the mitral valve 1 or its associated structure organically changes or functionally changes, for example, when the chordae tendineae 4 is partially ruptured, the anterior leaflet 1a and the posterior leaflet 1b of the mitral valve 1 are poorly conjoined. Thus, when the left ventricle 3 contracts, the mitral valve 1 cannot be fully closed, causing blood to regurgitate from the left ventricle 3 to the left atrium 2, thereby leading to a series of pathophysiological changes called "mitral regurgitation".

Transcatheter mitral valve clamping refers to implanting a valve clamping device into the mitral valve, and pulling the anterior and posterior leaflets toward each other by a pair of closeable clamp arms to reduce or eliminate valve leaflet gaps to treat the mitral regurgitation. In a valve clamping device of the prior art, an elastomer is added into both clamp arms, the valve leaflet of each side is clamped between a clamp arm of one side and one side of the elastomer, and the spacing of the valve leaflets is accommodated by deformation of the elastomer, thereby adjusting the degree of pulling of the clamp arms on the valve leaflets. The elastomer comprises a deformable mesh body, two ends of which are fixed with a head such as a steel sleeve and then fixed to a support rod between the two clamp arms. However, since the two ends of the elastomer are fixed by the head, when the clamp arm is closed, the head limits axial movement of the elastomer. The elastomer can only be compressed radially, which affects the deformation of the elastomer, thereby increasing the size of the clamping device in a delivery state, which is adverse to the passage of the clamping device in a tortuous vessel, and will cause the elastomer not to fully adhere to the valve leaflet after the implantation of the clamping device. That is, the valve clamping device of the prior art has poor conformability to valve leaflet physiological structure of different patients.

SUMMARY

In a first aspect, the present disclosure relates to a valve clamping device with an adjustable bearing force comprising:

a support portion comprising a connecting end and a free end disposed oppositely;

a hollow adjustment portion made of a shape memory material, wherein one end of the adjustment portion is sleeved outside the connecting end and connected to the support portion, and another end of the adjustment portion hangs in air;

a clamping portion enclosed outside the adjustment portion; and a driving portion connected to the clamping portion to drive the clamping portion to open or close around the adjustment portion;

wherein the free end of the support portion is within the adjustment portion, and a proximal end of the adjustment portion is spaced apart from a proximal end of the support portion.

In some embodiments, the adjustment portion is in an approximately cone shape in a natural state, a proximal end surface of the adjustment portion forms a bottom surface of a cone, and a connection end between the adjustment portion and the support portion forms an apex of the cone.

In some embodiments, the adjustment portion comprises a hanging extension, and the extension extends toward a proximal end direction and forms a circle of surrounding periphery of the adjustment portion.

In some embodiments, the adjustment portion comprises a hanging extension, and the extension extends in a radial direction away from the support portion and forms a circle of surrounding periphery of the adjustment portion.

In some embodiments, the adjustment portion comprises a plurality of first curved surfaces and a plurality of second curved surfaces, the first curved surface and the second curved surface are adjacent to each other, the two oppositely disposed first curved surfaces face the clamping portion respectively, and an area of the first curved surface is larger than an area of the second curved surface.

In some embodiments, a biocompatible membrane or a biocompatible coating is provided outside and/or inside the adjustment portion.

In some embodiments, the adjustment portion comprises an elastic body having a natural state and a compressed state, an end of the elastic body is connected to the support portion, another end of the elastic body has an opening, and a size of the opening is smaller than or equal to a size of the free end of the support portion when the elastic body is in the compressed state.

In some embodiments, a proximal end edge of the elastic body is enclosed to form the opening.

In some embodiments, a proximal end of the elastic body is folded and then provided with a head.

In some embodiments, the clamping portion comprises at least two clamp arms symmetrically disposed with respect to the adjustment portion, and the driving portion is connected to each of the clamp arms to drive each of the clamp arms to rotate about the adjustment portion.

In some embodiments, the valve clamping device further comprises a gripping portion that is disposed between the clamping portion and the adjustment portion, can be opened or closed with respect to the adjustment portion, and is at least partially located on an inner surface of the clamping portion when both the gripping portion and the clamping portion are opened.

In some embodiments, a biocompatible membrane is applied to an outside of both the clamp arm and the gripping portion.

In some embodiments, the valve clamping device further comprises a base fixedly connected to the support portion, and the clamping portion is rotatably connected to the base.

In some embodiments, the driving portion comprises: a drive shaft; a connection seat; and at least two connecting rods, wherein one end of each of the connecting rods is connected to the clamping portion and another end is pivotally connected to the connection seat; one end of the drive shaft is connected to the connection seat and another end movably penetrates the base.

In some embodiments, the valve clamping device further comprises a locking portion disposed in the base, which limits relative movement of the drive shaft and the base.

In a second aspect, the present disclosure relates to a valve clamping system comprising the valve clamping device with an adjustable bearing force and a delivery device, wherein the delivery device comprises: a pushing shaft having an axial length and a mandrel movably penetrating the pushing shaft, wherein the pushing shaft and the support portion are detachably connected, and the mandrel is connected to the driving portion to drive the clamping portion to open and close with respect to the support portion.

In a third aspect, the present disclosure relates to a method for repairing a valve, comprising:

pushing the drive shaft and the valve clamping device of the present disclosure connected thereto from an atrium of a subject in need thereof to a ventricle via a valve by a guiding device;

adjusting the valve clamping device to approach an anterior leaflet and a posterior leaflet of the valve;

unlocking the locking portion in the base, pulling a mandrel and the drive shaft to the proximal end, driving the clamp arm to open with respect to the support portion, and adjusting the direction of the clamp arm, so that the clamp arm is perpendicular to a matching line of the valve;

withdrawing the entire valve clamping device to the proximal end to cause the clamp arm to hold the valve leaflet on the ventricle side, and releasing gripping arms on both sides, wherein the gripping arm on each side presses the valve leaflet on the atrium side and fixes the valve leaflet in cooperation with the clamp arm on the side to realize complete clamping of the valve leaflet;

pushing the mandrel and the drive shaft to the distal end when the anterior leaflet and the posterior leaflet of the valve are clamped between the pair of clamp arms and the gripping arms respectively, thereby driving the clamp arms to close; and releasing threaded connection between the mandrel and the drive shaft and withdrawing the mandrel, so that two branches of a fixing member return to a state of converging to a center axis, a locking nose is disengaged from a detent of the support portion, and the valve clamping device is disconnected from a delivery device, and then withdrawing the delivery device from the body.

In some embodiments, the subject may be a human.

In some embodiments, the exemplary examples of the valve that can be used in the present disclosure includes, but is not limited to, mitral valve and tricuspid valve.

Some embodiments of the present disclosure have the following advantages: regarding the valve clamping device with an adjustable bearing force and the valve clamping system comprising the valve clamping device with an adjustable bearing force, one end of the adjustment portion is sleeved on the outside of the connecting end and is connected to the support portion and another end hangs freely. The freely hanging end is not connected to the support portion and the delivery device, and thus is no longer restricted by the support portion or the delivery device, which improves the axial deformation ability of the adjustment portion while enhancing the axial bending deformation ability thereof. Therefore, when the valve clamping device is radially compressed into a conveyor for in vivo delivery, the valve clamping device is not only easily compressed into a sheath, but can also accommodate blood vessels of different curvatures during delivery in the blood vessel, which facilitates passage of the conveyor in the blood vessel, thereby reducing damage to the blood vessel wall. In addition, after implantation of the valve clamping device with an adjustable bearing force, when the valve leaflet and the adjustment portion are clamped by a clamp arm, elastic fit of the valve leaflet to the adjustment portion can be improved due to unrestricted axial deformation of the adjustment portion, which improves conformability to valve leaflet physiological structure of different patients.

BRIEF DESCRIPTION OF THE DRAWINGS

The drawings herein are incorporated into the specification and constitute a part of the specification. The drawings show examples conforming to the present disclosure and are used together with the specification to explain the principle of the present disclosure.

In order to explain the technical solutions more clearly in the examples of the present disclosure or the prior art, the drawings used in the examples or the description of the prior art are briefly explained. Obviously, one skilled in the art can obtain other drawings based on these drawings without involving creative efforts.

5        6

Figures 3A, 3B:
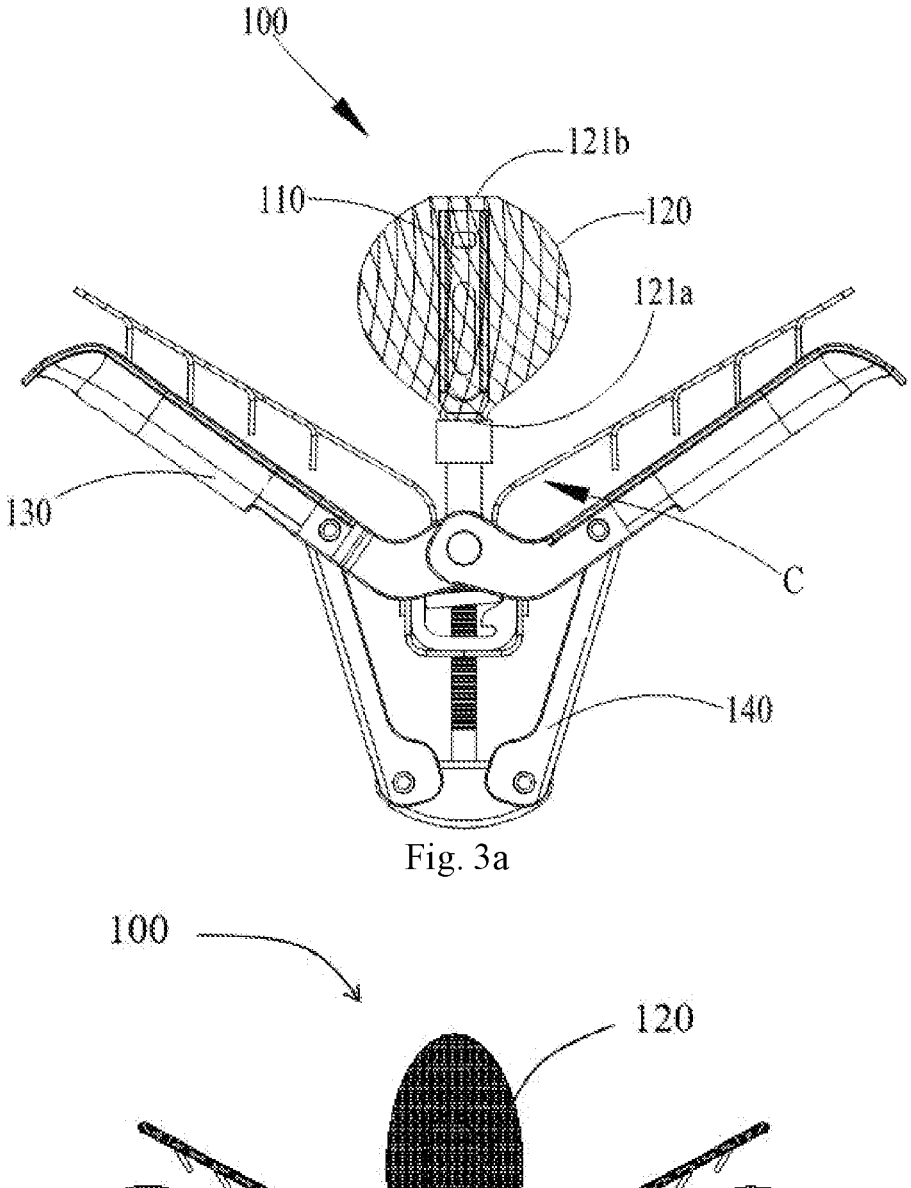
FIG. 3*a* shows a schematic structural diagram illustrating a valve clamping device with an adjustable bearing force of Example 1 of the present disclosure.
FIG. 3*b* shows a schematic structural diagram illustrating the valve clamping device with an adjustable bearing force of FIG. 3*a* to which a biocompatible membrane is applied.
Figure 7:
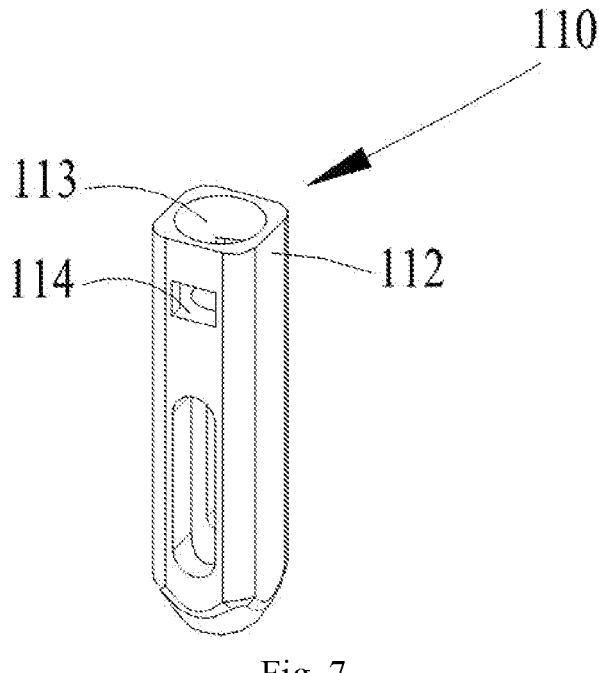

FIG. 7 shows a schematic structural diagram illustrating the support portion in FIG. 3*a;*

Figure 8:
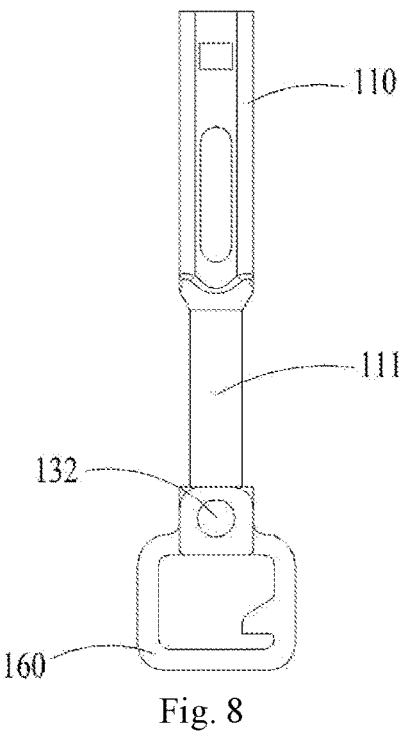

FIG. 8 shows a schematic structural diagram illustrating the support portion mated with a base in FIG. 3*a;*

Figure 9:
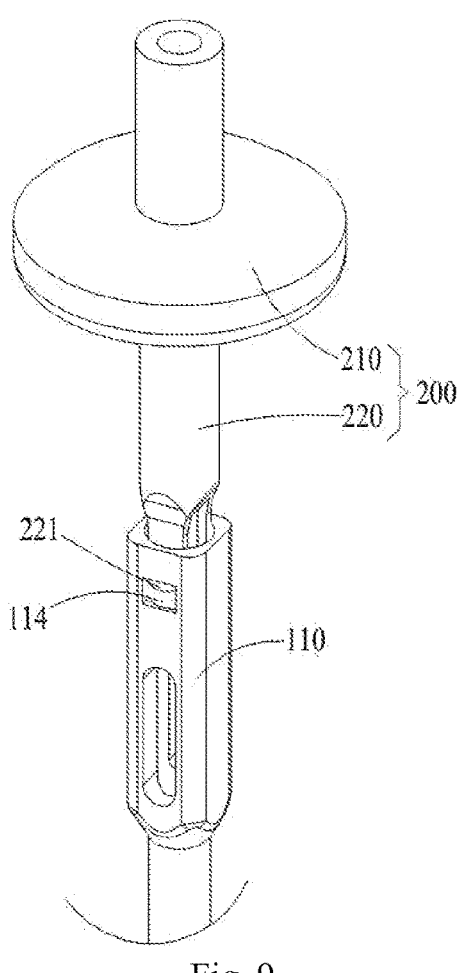

FIG. 9 shows a schematic structural diagram illustrating the support portion of the valve clamping device with an adjustable bearing force of FIG. 3*a* mated with a delivery device;

FIGS. 10 to 14 show schematic diagrams illustrating a delivery process of anterogradely approaching and repairing a mitral valve via a left atrium using the valve clamping device with an adjustable bearing force of FIG. 3*a;*

Figure 15:
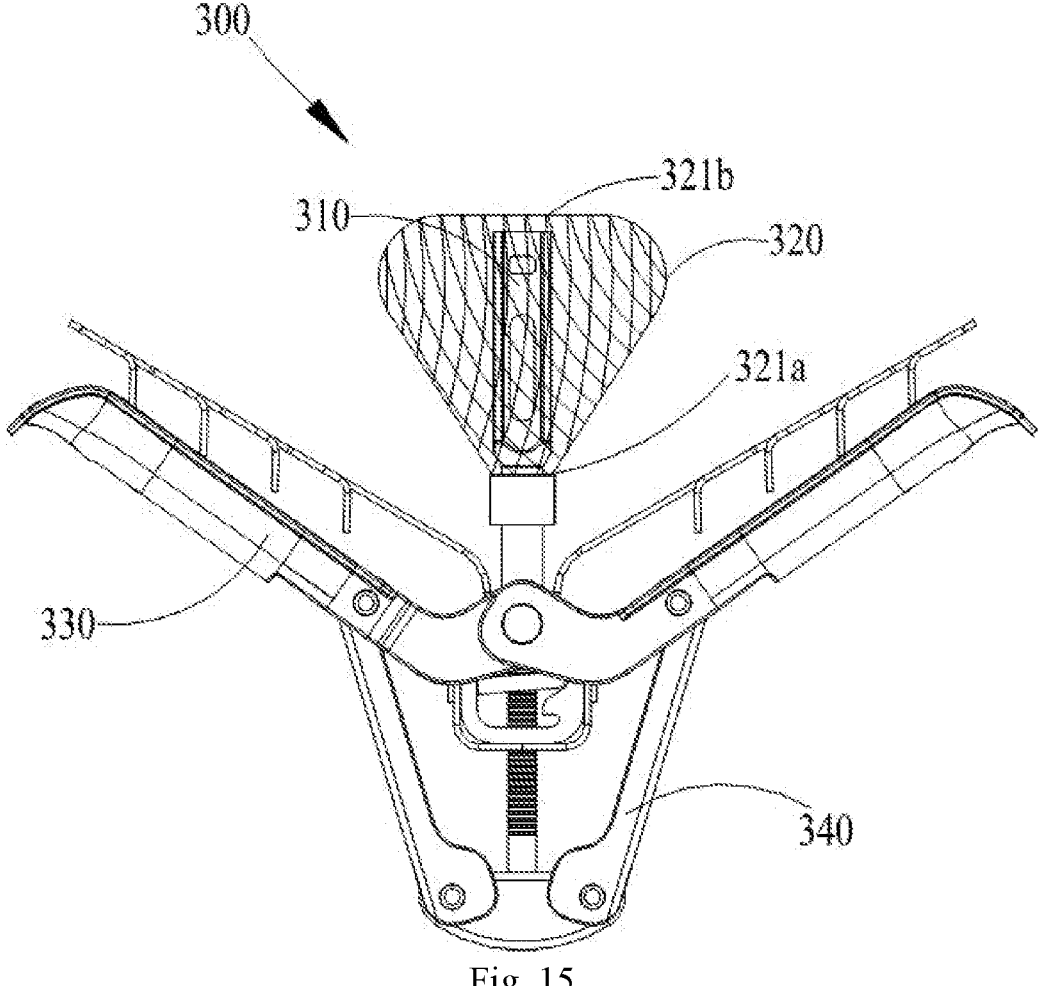
Figure 16:
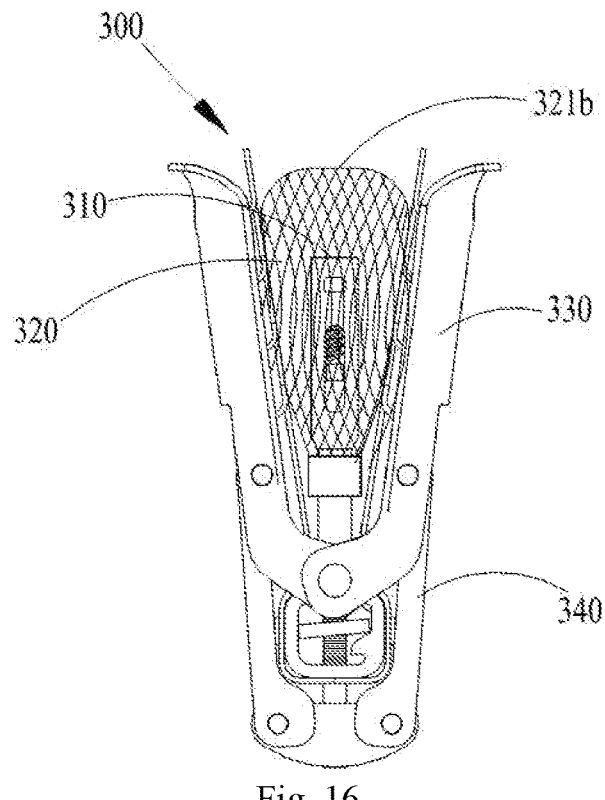
Figure 17:
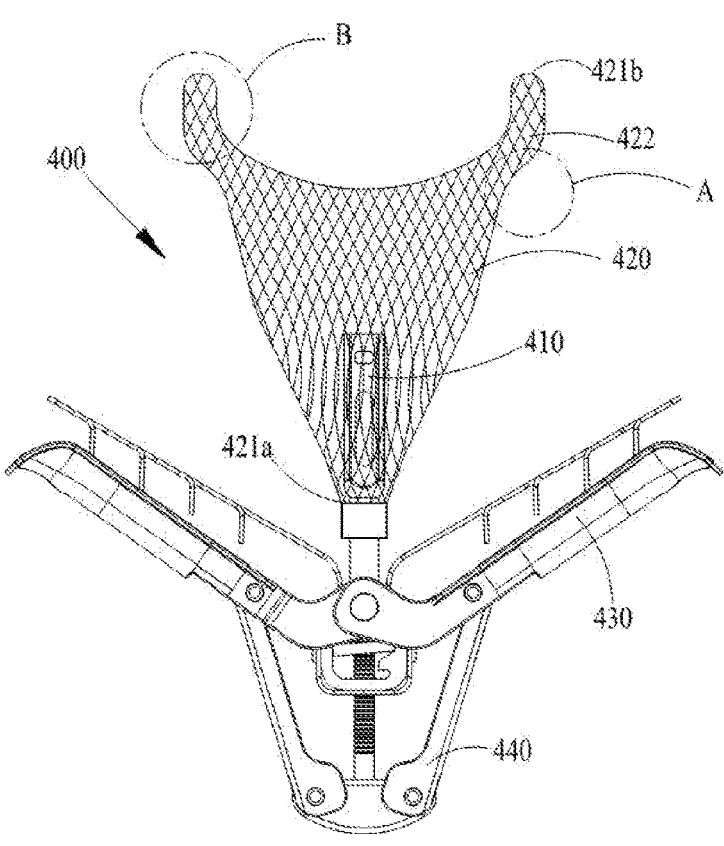
Figure 18:
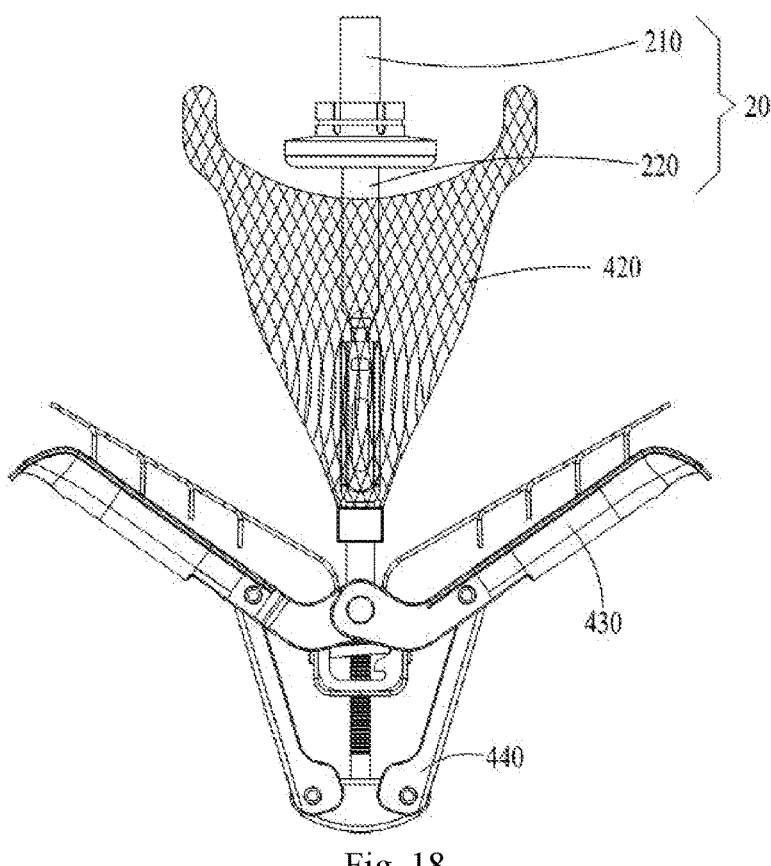
Figure 19:
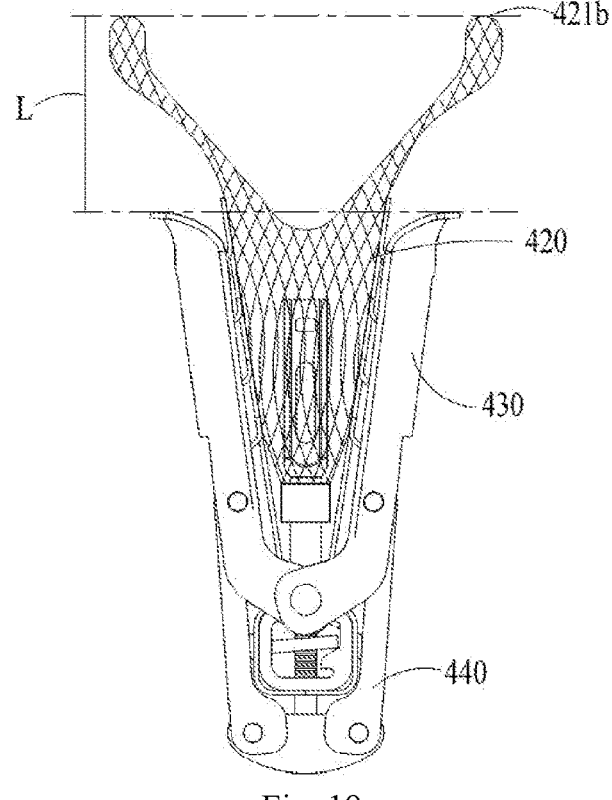
Figure 20:
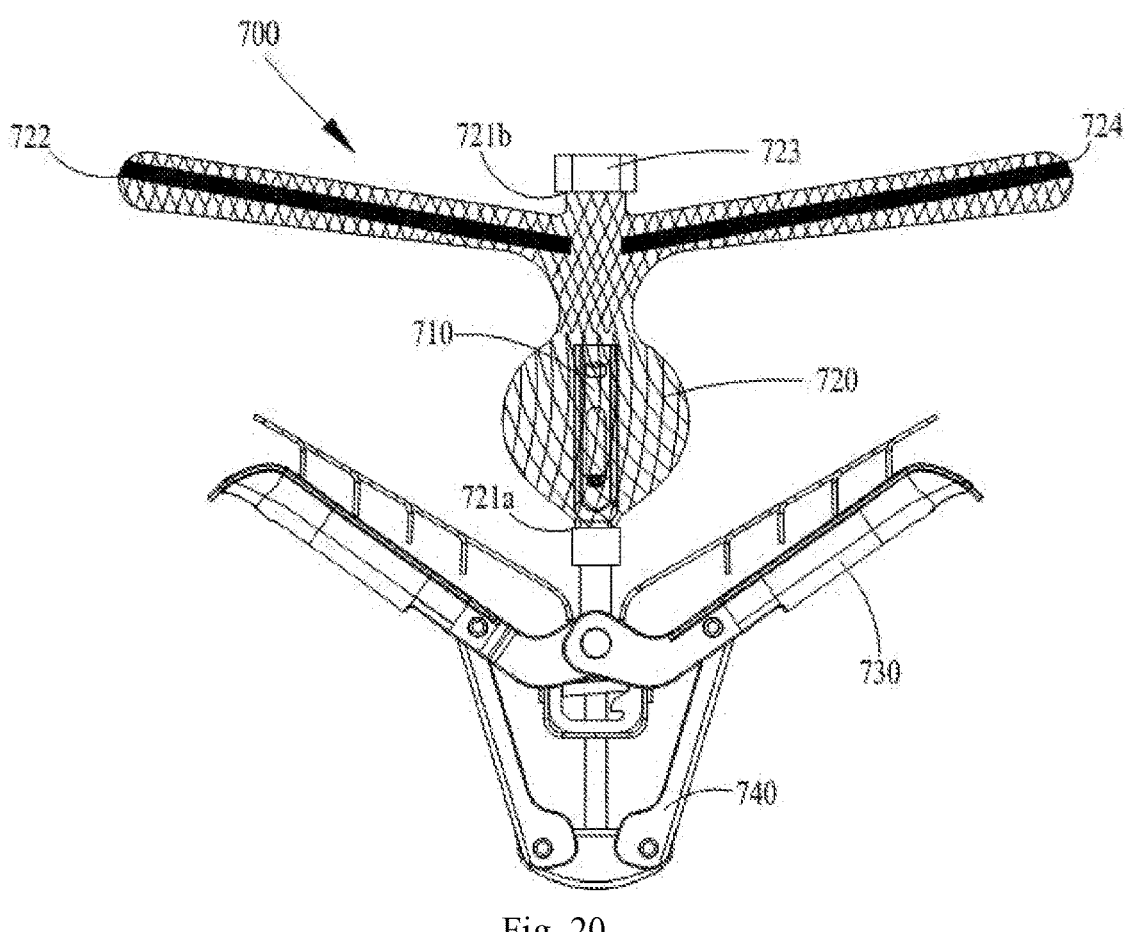
Figure 21:
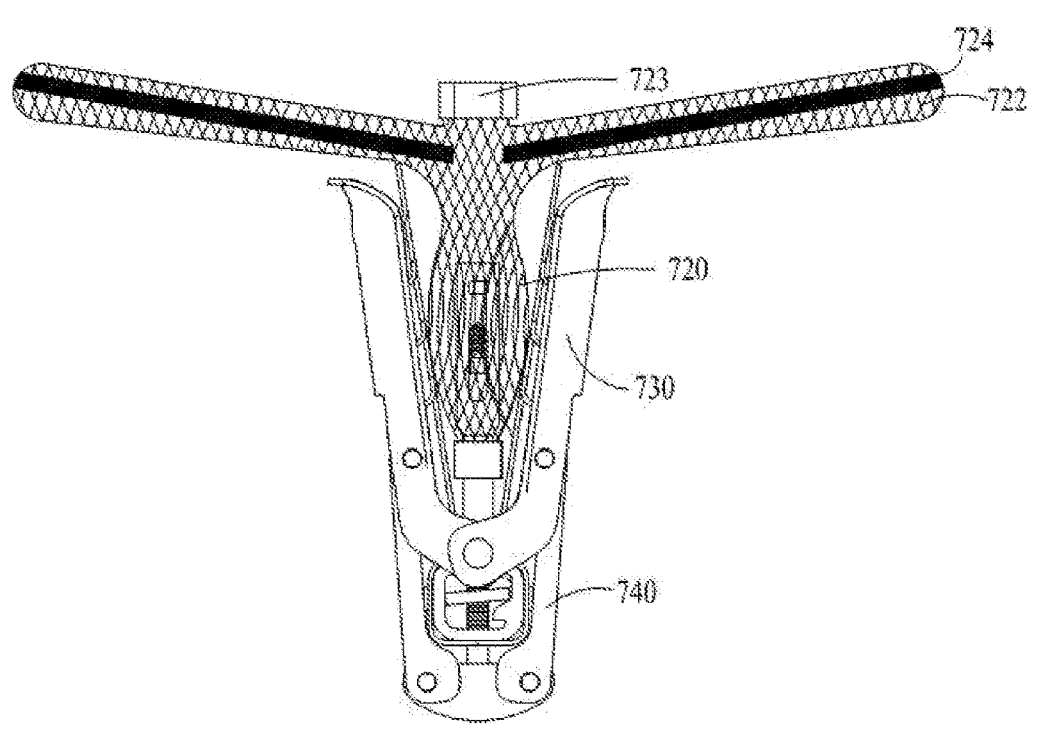
Figure 25:
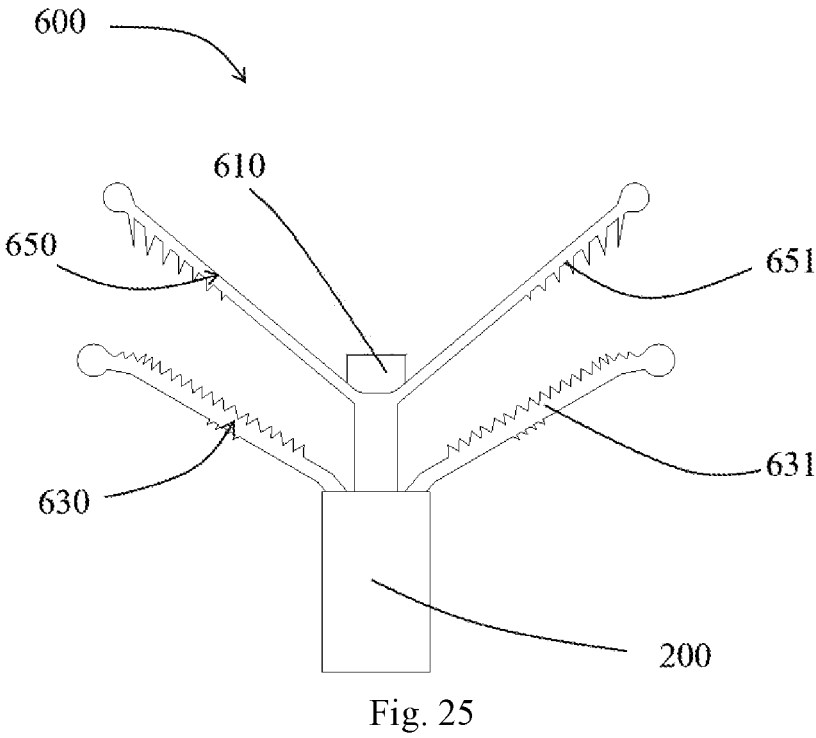
Figure 26:
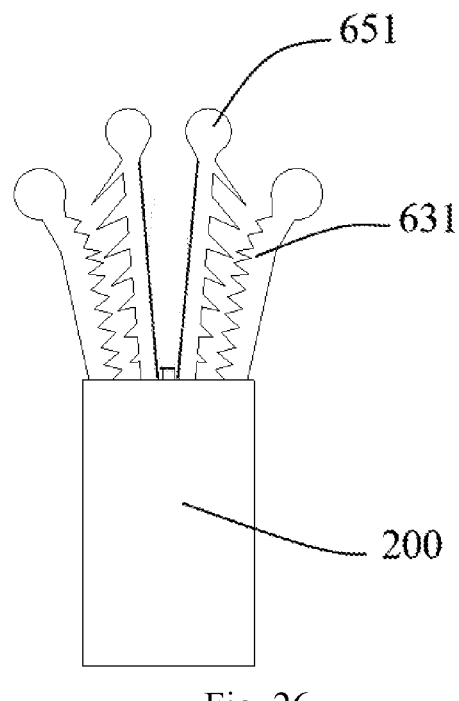

FIG. 15 shows a schematic structural diagram illustrating a valve clamping device with an adjustable bearing force of Example 2 of the present disclosure;

FIG. 16 shows a schematic structural diagram illustrating the valve clamping device with an adjustable bearing force of Example 2 of the present disclosure in a closed state;

FIG. 17 shows a schematic structural diagram illustrating a valve clamping device with an adjustable bearing force of Example 3 of the present disclosure;

FIG. 18 shows a schematic structural diagram illustrating the valve clamping device with an adjustable bearing force of Example 3 of the present disclosure which is mated with a delivery device;

FIG. 19 shows a schematic structural diagram illustrating the valve clamping device with an adjustable bearing force of Example 3 of the present disclosure in a closed state;

FIG. 20 shows a schematic structural diagram illustrating a valve clamping device with an adjustable bearing force of Example 4 of the present disclosure;

FIG. 21 shows a schematic structural diagram illustrating the valve clamping device with an adjustable bearing force of Example 4 of the present disclosure in a closed state;

FIG. 22 shows a schematic structural diagram illustrating a first curved surface side of an adjustment portion of a valve clamping device with an adjustable bearing force of Example 5 of the present disclosure;

FIG. 23 shows a top view of the adjustment portion of FIG. 22;

FIG. 24 shows a schematic structural diagram illustrating a second curved surface side of the adjustment portion of FIG. 22;

FIG. 25 shows a schematic structural diagram illustrating a valve clamping device with an adjustable bearing force of Example 6 of the present disclosure; and FIG. 26 shows a schematic structural diagram illustrating the valve clamping device with an adjustable bearing force of FIG. 25 radially compressed and then partly received in a delivery device.

DETAILED DESCRIPTION

The technical solutions of the present disclosure are described below clearly and completely with reference to the drawings. Obviously, the described are only part of examples of the present disclosure, rather than all of the examples. Based on the examples in the present disclosure, all other examples obtained by one skilled in the art without involving inventive work fall within the protection scope of the present disclosure. In the description of the present disclosure, it is noted that an orientation or position relationship indicated by the terms "upper", "lower", "inner", "outer", and the like is based on an orientation or position relationship shown in the drawings, which is merely for convenience of describing the present disclosure and simplifying the description, rather than indicating or implying that the device or element being referred to must have a particular orientation or be constructed and operated in a particular orientation, and thus, should not be construed as limiting the disclosure. Moreover, the terms "first", "second", and the like are used for descriptive purposes only and should not be construed as indicating or implying relative importance.

In the description of the present disclosure, it is noted that in the field of interventional medical devices, a proximal end refers to an end close to an operator, and a distal end refers to an end far from the operator; an axial direction refers to a direction parallel to a line between the center of the distal end and the center of the proximal end of the medical device. The foregoing definitions are for convenience of description only and should not to be construed as limiting the present disclosure.

Referring to FIG. 3*a* to FIG. 14, a valve clamping device 100 with an adjustable bearing force of Example 1 of the present disclosure comprises: a support portion 110 comprising a connecting end 111 and a free end 112 disposed oppositely; a hollow adjustment portion 120 made of a shape memory material, one end of which is sleeved outside the connecting end 111 and connected to the support portion 110, and another end of which hangs in air, wherein the free end 112 of the support portion 110 hangs within the adjustment portion 120, and the proximal end of the adjustment portion 120 is spaced apart from the free end 112; a clamping portion 130 enclosed outside the adjustment portion 120; and a driving portion 140 connected to the clamping portion 130 to drive the clamping portion 130 to open or close around the adjustment portion 120.

One end of the adjustment portion 120 of the valve clamping device 100 with an adjustable bearing force is a freely hanging end 121*b*, and the freely hanging end 121*b* is no longer restricted by the support portion 110 or a delivery device 200, which improves the axial deformation ability of the adjustment portion 120 while enhancing the axial bending deformation ability thereof. Therefore, when the valve clamping device 100 with an adjustable bearing force is radially compressed into a conveyor for in vivo delivery, the valve clamping device 100 is not only easily compressed into a sheath, but can also accommodate blood vessels of different curvatures during delivery in the blood vessel, which facilitates passage of the conveyor in the blood vessel, thereby reducing damage to the blood vessel wall.

At the same time, the free end 112 is connected to or detached from the delivery device within the adjustment portion 120, and collision of the free end 112 with the blood vessel or other tissues is avoided during the detachment process of the device, which reduces damage to the body tissue, and prevents the free end 112 from hooking the chordae tendineae and causes failure in detachment.

In some embodiments, after an implantation of the valve clamping device 100 with an adjustable bearing force, when the valve leaflet and the adjustment portion 120 are clamped by a clamp arm 131, elastic fit of the valve leaflet to the adjustment portion 120 can be improved due to unrestricted axial deformation of the adjustment portion 120, which improves conformability to valve leaflet physiological structure of different patients.

In some embodiments, after implantation of the valve clamping device 100 with an adjustable bearing force, the free end 112 hangs within the adjustment portion 120, and the proximal end of the adjustment portion 120 is spaced apart from the free end 112, which can avoid interference or wrapping of the free end 112 with the freely hanging end 121*b* of the adjustment portion 120, thereby ensuring safe implantation of the device.

The valve clamping device 100 with an adjustable bearing force mainly comprises two states: an open state and a closed state. During a closing process of the clamping portion 130 around the adjustment portion 120, the adjustment portion 120 is radially compressed, and a spacing h between the proximal end of the adjustment portion 120 and the proximal end of the support portion 110 gradually increases. That is, one end 121*a* of the adjustment portion 120 is sleeved outside the connection end and connected to the support portion 110, another end of the adjustment portion 120 is a freely hanging end 121*b*, and while the clamping portion 130 compresses the adjustment portion 120, the freely hanging end 121*b* of the adjustment portion 120 moves toward the proximal end and the spacing h with the support portion 110 increases.

Figure 6:
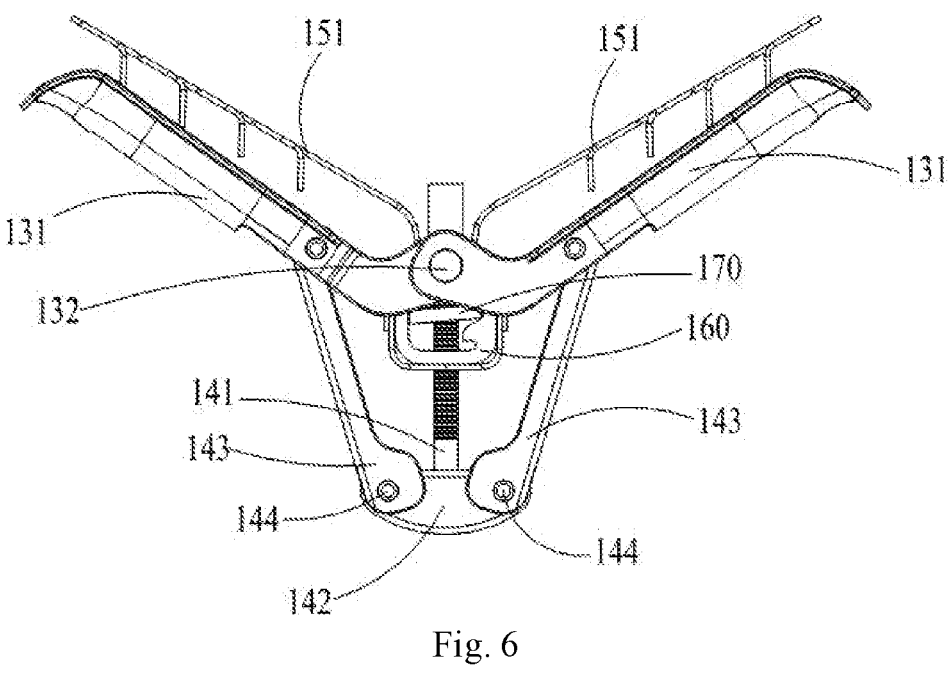
FIG. 6 shows a schematic structural diagram illustrating the clamping portion and the driving portion in FIG. 3*a* in combination.

Referring to FIG. 6 to FIG. 8, the support portion 110 may be a circular tube body, a square column tube body, an oblate tube body, or the like with both ends axially penetrating. A circular tube body is used in the present example, a distal end of the circular tube body is the connection end 111, a proximal end thereof is the free end 112. At least a part of the support portion 110 is disposed within a hollow of the adjustment portion 120, for example, the free end 112 of the support portion 110 is positioned within the adjustment portion 120, and the free end 112 is positioned within the adjustment portion 120 in both the closed state and the open state without being exposed outside the adjustment portion 120. The support portion 110 is also provided with an axial through-hole-shaped penetrating channel 113 to cooperate and mate with the driving portion 140 and the delivery device 200. At least two detents 114 are provided on the tube wall of the circular tube body of the support portion 110 for detachable connection with the delivery device 200. For example, a locking nose 221 on the delivery device 200 snaps into the detent 114, then the delivery device 200 is in snap connection with the support portion 110, and can deliver the valve clamping device 100. The delivery device 200 is separated from the valve clamping device 100 when the locking nose 221 is disengaged from the detent 114. The structure of the support portion 110 herein is only an example and does not limit the present disclosure. Other structures of the support portion 110 used by one skilled in the art based on teachings of the present disclosure are within the scope of the present disclosure.

Whether in the closed state or the open state, the proximal free end 112 of the valve clamping device 100 with an adjustable bearing force of Example 1 is within the hollow adjustment portion 120, and thus is always not exposed to the delivery device 200 or exposed to the heart, thereby avoiding flushing of blood and minimizing formation of thrombus after implantation. Direct contact with the valve leaflet is also avoided after implantation, along with long term pulsation of the valve leaflet, wear and even perforation of the valve leaflet are avoided, and implantation safety is improved.

Figure 4:
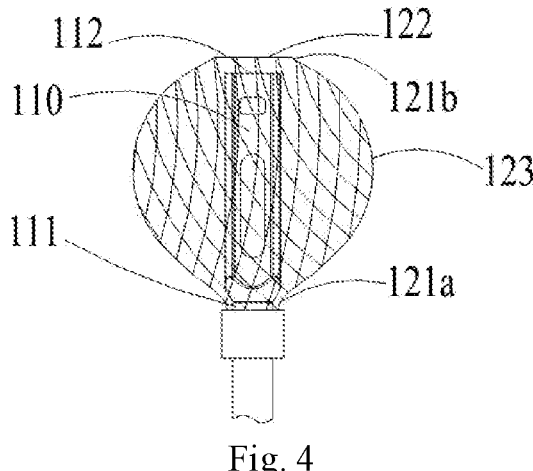
FIG. 4 shows a schematic structural diagram illustrating the adjustment portion and the support portion in FIG. 3*a* in combination.

Referring to FIG. 4 and FIG. 8, the adjustment portion 120 comprises a deformable elastic body 123 having a natural state and a compressed state and comprising a hollow accommodating cavity in which at least a part of the support portion 110 is disposed. One end 121*a* of the elastic body 123 is connected to the support portion 110, another end 121*b* of the elastic body 123 has an opening 122 and freely hangs. In the compressed state, the size of the opening 122 is less than or equal to the size of the free end of the support portion 110. Therefrom, the size of the opening 122 decreases to prevent the support portion 110 from exposing from the opening 122 when the valve clamping device 100 is closed and the elastic body 123 is squeezed. The elastic body 123 can deform so as to accommodate spacing between different valve leaflets and adjust a pulling degree of the valve leaflet by the valve clamping device 100. The opening 122 of the elastic body 123 is used for penetrating the distal end of the delivery device 200. It is to be understood that the distal end of the delivery device 200 penetrates the hollow accommodating cavity of the elastic body 123 through the opening 122 and then is connected to the proximal end (free end) of the support portion 110, while the opening 122 at the distal end of the elastic body 123 is disconnected from the distal end of the delivery device 200 or the proximal end (free end) of the support portion 110, that is, the proximal end 121*b* of the elastic body 123 is in a freely hanging state. Thus, in a delivery process or a process of clamping the valve leaflet, when the clamping portion 130 is closed, the elastic body 123 in the adjustment portion 120 is not restricted by the support portion 110 or the delivery device 200 and is deformable in the radial direction and the axial direction. The degree of deformation is larger, which is more conducive to delivery and has stronger ability to accommodate the valve leaflets; when the connection between the distal end of the delivery device 200 and the proximal end (free end) of the support portion 110 is detached, the deformation ability of the freely hanging end of the adjustment portion 120 is stronger, and the ability to accommodate the valve leaflet is stronger.

The adjustment portion 120 comprises a proximal end and a distal end, and in some embodiments, a hollow enclosing structure (not shown) is sleeved on a proximal edge of the elastic body 123 to form an opening, that is, the proximal end of the elastic body 123 is folded and then provided with a head. The enclosing structure may be annular or polygonal, may be made of a hard material such as stainless steel, so that wires of a mesh structure or struts of a frame structure are properly folded toward the central axis, but not closed, so as to form the opening 122 at the center of the enclosing structure. In some embodiments, the proximal edge of the elastic body 123 is enclosed to form the opening 122, the size of the opening 122 is less than or equal to the size of the free end 112, thereby ensuring that the free end 112 of the support portion 110 does not extend out of the adjustment portion 120 in both the compressed state and the natural state.

The proximal edge of the elastic body 123 is enclosed to form the opening 122, the proximal head of the adjustment portion 120 of the valve clamping device 100 is eliminated, and when the clamping portion 130 is closed, the elastic body 123 can be deformed in both the radial and axial directions to a large extent, which is more conducive to delivery; the elastic body 123 is not restricted by axial movement of each wire or strut thereof restricted by the head, and thus can be moderately crimped or bent to fully abut the valve leaflet and better accommodate the physiological structure of the valve leaflets of different patients; the risk that a proximal head member in the prior art falls off after implantation for a period of time can also be avoided; the distal end of the elastic body 123 is connected to the support portion 110, and the proximal opening 122 opens, so the center of gravity of the elastic body 123 is always located in the axial direction (i.e., an axial line of the elastic body 123) of the support portion 110, so that the elastic body 123 has good self-centrality and is not easy to tilt.

Figure 5:
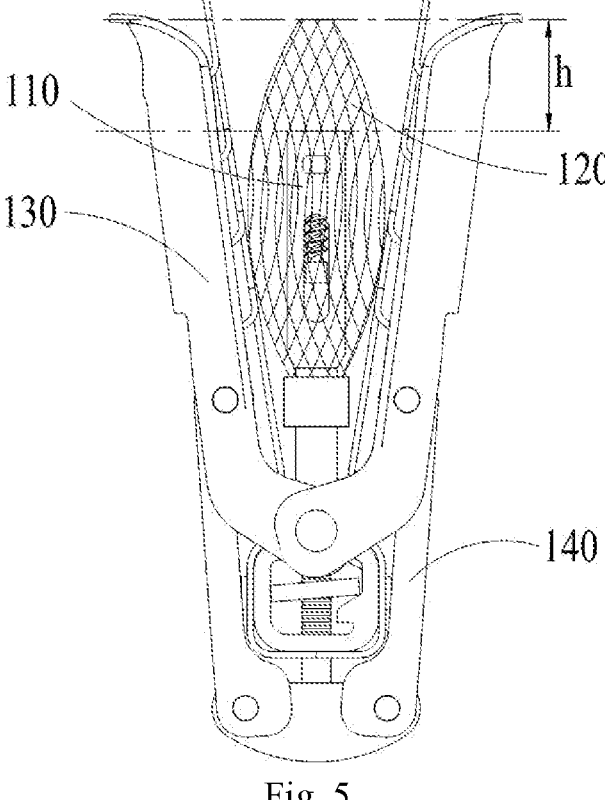
FIG. 5 shows a schematic structural diagram illustrating the valve clamping device with an adjustable bearing force of FIG. 3*a* in a closed state.

Referring to FIG. 5, the clamping portion 130 comprises at least two clamp arms 131, and generally may comprise at least one set of clamp arms 131, each set comprising two clamp arms 131 disposed symmetrically with respect to the adjustment portion 120, and the clamping portion 130 in the drawing comprises a set of clamp arms 131. This is only an example, and one skilled in the art may select a suitable number of the clamp arms 131 as needed, such as two or more sets of clamp arms. The driving portion 140 is connected to each of the clamp arm 131, for example, the driving portion 140 is connected to two clamp arms 131 in one set of clamp arms 131, to drive each of the clamp arms 131 to rotate about the adjustment portion 120. In some embodiments, three or more clamp arms 131 may be provided in each set as needed, for example, three valve leaflets of a tricuspid valve may be clamped by the three clamp arms 131 which can be opened and closed relatively, thereby treating tricuspid regurgitation.

In the delivery state, the driving portion 140 drives the clamp arm 131 to close around the adjustment portion 120, thereby reducing the outer diameter of the valve clamping device 100 and facilitating delivery; after the opening of the valve clamping device 100 in vivo, the driving portion 140 drives the clamp arm 131 to clamp the valve leaflet between the clamp arm 131 and the adjustment portion 120 to realize valve leaflet clamping.

In some embodiments, the valve clamping device 100 further comprises a gripping portion, and may generally comprise at least one set of gripping arms 151, each set comprising two gripping arms 151 disposed symmetrically with respect to the adjustment portion 120. The gripping portion (e.g., gripping arms 151) is disposed between the clamping portion 130 (e.g., the clamp arm 131) and the adjustment portion 120 and can be opened or closed with respect to the adjustment portion 120, and the gripping portion is at least partially located on the inner surface of the clamping portion 130. In some embodiments, three or more gripping arms 151 may also be provided in each set as needed to mate with the clamp arm 131 to realize the gripping function.

In the delivery state, the gripping portion is at least partially received in the inner surface of the clamping portion 130, that is, the gripping arm 151 is at least partially received in the inner surface of the clamp arm 131, thereby reducing the outer diameter of the valve clamping device 100 and facilitating delivery; after the clamp arm 131 cooperates with the gripping arm 151 to clamp the valve leaflet, the concave inner surface may increase the contact area between the clamp arm 131 and the valve leaflet, and causes the gripping arm 151 to press the valve leaflet into the inner surface of the clamp arm 131, thereby increasing a clamping force on the valve leaflet.

Referring to FIG. 3*b*, a biocompatible membrane or a biocompatible coating is applied to the outside of both the clamp arm 131 and the gripping portion, which makes the valve clamping device 100 more biocompatible.

Referring to FIG. 8, the valve clamping device 100 further comprises a base 160 fixedly connected to the support portion 110, and the clamping portion 130 is rotatably connected to the base 160. In some embodiments, the proximal end of the base 160 is fixedly connected to the distal end 121*a* of the support portion 110. It should be noted that this part is defined as a term "base" for convenience of description, and a structure that realizes the function of the base 160 may also be the distal end of the support portion 110, i.e., an integral structure formed with the support portion 110. Thus, defining the term "base" should not limit the scope of the present disclosure. The clamp arms 131 in each set are connected together by a pivot 132 on the base 160, so that each clamp arm 131 cooperate with each other to open and close together around the adjustment portion 120 under the driving of the driving portion 140.

Still referring to FIG. 6 and FIG. 8, the driving portion 140 comprises: a drive shaft 141, a connection seat 142, and two connecting rods 143; wherein one end of each connecting rod 143 is connected to the clamping portion 130 and another end is pivotally connected to the connection seat 142; one end of the drive shaft 141 is connected to the connection seat 142 and another end movably penetrates the base 160. In some embodiments, one end of each connecting rod 143 is connected to a clamp arm 131 and another end is connected to the connection seat 142 by a pivot 144, that is, each clamp arm 131 is rotatably connected to the distal end of the connection seat 142 of the drive shaft 141 by the connecting rod 143 on a corresponding side. The drive shaft 141 movably penetrates the base 160, and as the drive shaft 141 slides axially with respect to the base 160, the connecting rod 143 rotates and drives the clamp arm 131 to open and close with respect to the base 160.

In some embodiments, the driving portion 140 comprises at least one set of connecting rods 143, and the number of the connecting rods 143 is set in one-to-one correspondence with the setting of the clamp arms 131. For example, two clamp arms 131 are used in the drawing, and two cooperating connecting rods 143 are set correspondingly. The distal end of the connecting rod 143 is rotatably connected to the connection seat 142 at the distal end of the drive shaft 141 by a rotation pin or bolt 144 or the like. As the drive shaft 141 axially slides to the distal end with respect to the base 160, it drives the connecting rod 143 to move, and under pulling of the connecting rod 143, the clamp arm 131 rotates about a pin hole 144 and opens with respect to the base 160. As the drive shaft 141 axially slides to the proximal end with respect to the base 160, the connecting rod 143 pulls the clamp arm 131 to rotate about the pin hole 144 and close with respect to the base 160.

The connection seat 142 is fixedly disposed at the distal end of the drive shaft 141 by welding or the like, and the connection seat 142 is provided with a pair of pins. The pin hole is used to hingedly connect the connecting rod 143 by the pin 144, and another end of the connecting rod 143 connects the clamp arm 131 to open and close the clamp arm 131 with respect to the base 160. The shape of the connection seat 142 is any structure such as a hemisphere, a spherical crown, or a bullet shape to allow the valve clamping device 100 to be more easily pushed in the body. The drive shaft 141 and the connection seat 142 may be an integral structure or a non-integral structure. To ensure safety after implantation, the drive shaft 141 and the connection seat 142 are made of a biocompatible material such as polyester, silicone, stainless steel, cobalt alloy, cobalt chromium alloy, or titanium alloy, and stainless steel or cobalt chromium alloy with a high hardness in some embodiments.

In some embodiments, referring to FIG. 6, the valve clamping device 100 further comprises a locking portion 170 disposed in the base 160, which limits relative movement of the drive shaft 141 and the base 160. In the delivery state, the locking portion 170 restricts the relative movement of the drive shaft 141 and the base 160, thereby ensuring that the clamping portion 130 remains in a closed state with respect to the adjustment portion 120 and the support portion 110 and avoiding accidental open of the clamping portion 130; after reaching the vicinity of the mitral valve, the restriction of the locking portion 170 on the drive shaft 141 is unlocked, that is, the clamping portion 130 can be driven by the driving portion 140 to open with respect to the adjustment portion 120 and the support portion 110 and bear the valve leaflet. Any existing suitable locking portion may be used and is not described in detail herein.

Referring to FIG. 6 and FIG. 9, the valve clamping system of the present example comprises the above-mentioned valve clamping device 100 and the delivery device 200, wherein the delivery device 200 comprises: a pushing shaft 210 having an axial length and a mandrel (not shown) movably penetrating the pushing shaft 210, wherein the pushing shaft 210 and the support portion 110 are detachably connected, and the mandrel is connected to the driving portion 140 to drive the clamping portion 130 to open and close with respect to the support portion 110. In some embodiments, the proximal end of the drive shaft 141 is provided with external threads, and the mandrel and the drive shaft 141 are threadedly connected to control axial movement of the drive shaft 141 by the mandrel outside the patient's body. What is described herein is only a part of the structure of the delivery device, other parts may use any existing suitable structure, which is not described in detail herein.

In some embodiments, a proximal outer wall of the support portion 110 is symmetrically provided with at least one detent 114 in communication with the tube cavity of the support portion 110, the distal end of the pushing shaft 210 is provided with a fixing member 220 that comprises two branches, and the end of each branch is a bulged locking nose 221. In a natural state, both branches point to the central axis of the fixing member 220. During assembly, the fixing member 220 is inserted into the support portion 110, and then the mandrel of the delivery device 200 is inserted into the pushing shaft 210, until the mandrel is inserted into the fixing member 220 to lift the two branches of the fixing member 220 outward. The locking nose 221 at the branch end snaps into the two detents 114 of the support portion 110, thereby connecting the support portion 110 to the fixing member 220, that is, connecting the valve clamping device 100 and the delivery device 200. When the mandrel is withdrawn from the fixing member 220 and the pushing shaft 210, the two branches restore an inward natural state, the locking nose 221 is disengaged from the detent 114 of the support portion 110, so that the valve clamping device 100 is disconnected from the delivery device 200. The fixing member 220 is made of a material with certain hardness and elasticity, such as nickel or titanium. The pushing shaft 210 may use a multilayer composite tube body. The mandrel is made of stainless steel material or a nickel titanium alloy material.

The inside of the support portion 110 is provided with a through hole as the penetrating channel 113 of the drive shaft 141, and the drive shaft 141 is axially and slidably disposed in the penetrating channel 113 of the support portion 110. The proximal end of the drive shaft 141 is provided with external threads for connection with the mandrel of the delivery device 200 to control axial movement of the drive shaft 141 by the mandrel. After the clamping portion 130 and the gripping portion 150 cooperate and clamp the valve tissue, the drive shaft 141 is driven to move axially to the proximal end by the mandrel, the drive shaft 141 drives the connecting rod 143 to rotate, and the connecting rod 143 drives the clamp arm 131 to fold with respect to the support portion 110 until the clamp arm 131 is fully closed with respect to the support portion 110. Therefore, the valve clamping device 100 is in a folded and closed state and hangs below the valve. Thereafter, the mandrel can be disconnected from the drive shaft 141, the mandrel is withdrawn backwards from between the fixing members 220, and the locking nose 221 is disengaged from the detents 114 of the support portion 110, thereby realizing detachment of the valve clamping device 100 from the delivery device 200. During the detachment process, since the connection site (i.e., the detachment site) between the valve clamping device 100 and the delivery device 200 is located within the adjustment portion 120 of the valve clamping device 100, the proximal end of the adjustment portion 120 is provided with an open opening 122, and no component may hook the locking nose 221 at the branch end of the fixing member 220, thus facilitating release of the valve clamping device 100. In addition, the detachment site is disposed in the adjustment portion 120 and is not directly flushed by blood, which can avoid mechanism failure at the detachment site and can reduce the risk of thrombosis.

Referring to FIG. 9 to FIG. 13, a use process of the valve clamping device 100 of the present disclosure is explained taking anterograde approach and repair of the mitral valve via the left atrium as an example.

Figure 10:
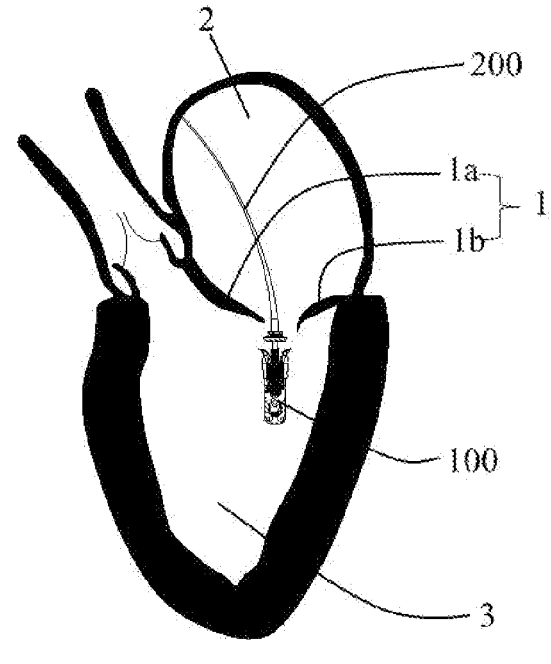
Figure 11:
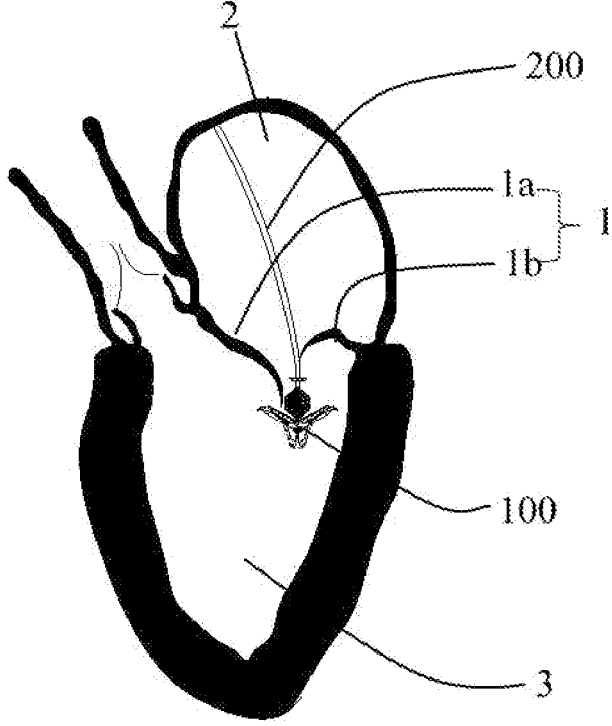
Figure 12:
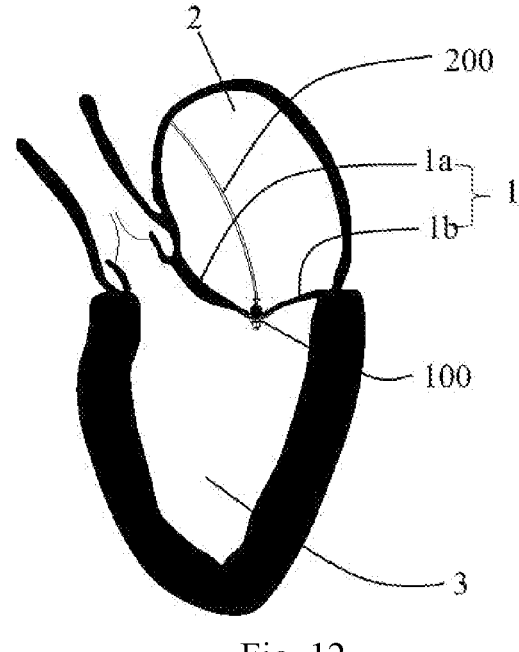
Figure 13:
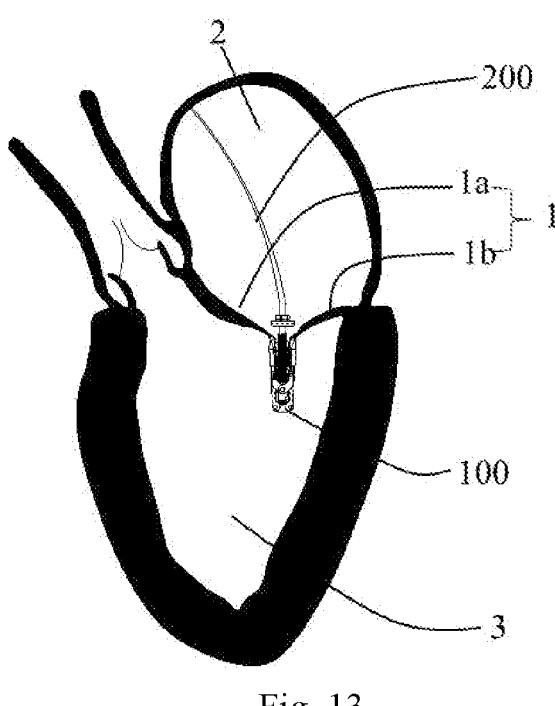
Figure 14:
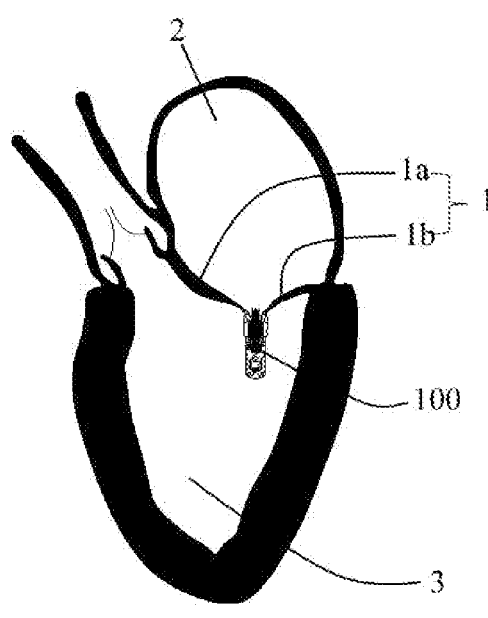

Step 1: pushing the drive shaft 141 and the valve clamping device 100 connected thereto from the left atrium 2 to the left ventricle 3 via the mitral valve 1 by a guiding device (not shown) such as an adjustable curved sheath, as shown in FIG. 9;

Step 2: adjusting the valve clamping device 100 to approach the anterior leaflet 1a and the posterior leaflet 1b of the mitral valve 1;

Step 3: unlocking a locking portion in the base 160, pulling the mandrel and the drive shaft 141 to the proximal end, driving the clamp arm 131 to open with respect to the support portion 110, and adjusting the direction of the clamp arm 131, at which time a relative position of the clamp arm 131 and the anterior and posterior leaflets 1a, 1b of the mitral valve 1 can be observed by an X-ray device so that the clamp arm 131 is perpendicular to a matching line of the mitral valve 1, as shown in FIG. 10;

Step 4: withdrawing the entire valve clamping device 100 to the proximal end to let the clamp arm 131 hold the valve leaflet 1 on the left ventricular 3 side, and releasing the gripping arms 151 on both sides, wherein the gripping arm 151 on each side presses the valve leaflet 1 on the atrium side and fixes the valve leaflet 1 with the clamp arm 131 on the side to realize complete clamping of the valve leaflet 1, as shown in FIG. 11;

Step 5: pushing the mandrel and the drive shaft 141 to the distal end when the anterior leaflet 1a and the posterior leaflet 1b of the mitral valve 1 are clamped between the pair of clamp arms 131 and the gripping arms 151 respectively, thereby driving the clamp arms 131 to close, as shown in FIG. 12;

Step 6: releasing the threaded connection between the mandrel and the drive shaft 141 and withdrawing the mandrel, so that the two branches of the fixing member 220 returns to a state of converging to the center axis, the locking nose 221 is disengaged from the detent 114 of the support portion 110, and the valve clamping device 100 is disconnected from the delivery device 200, and then withdrawing the delivery device 200 from the body, resulting in an implanted state as shown in FIG. 13, at which time the valve clamping device 100 pulls the anterior leaflet 1a and the posterior leaflet 1b of the mitral valve 1 toward each other to obtain a double orifice mitral valve and complete edge-to-edge repair of the mitral valve.

After implantation of the valve clamping device 100, the elastic adjustment portion 120 is filled between the anterior leaflet 1a and the posterior leaflet 1b of the clamped mitral valve 1 and abuts on the clamp arm 131, the elastic body 123 of the adjustment portion 120 (e.g., a mesh structure or a porous structure) has a cushioning effect on the pulsing valve leaflet 1, thereby realizing an adjustable pulling degree of the valve leaflet 1 by the valve clamping device 100 to avoid damage to the valve leaflet 1; the elastic body 123 can be squeezed and deformed by the pulse of the valve leaflet 1, the resulting elastic force pushes a part of the valve leaflet 1 close to the elastic body 123 in a direction away from the base 160, at which time a clamping angle between the anterior leaflet and the posterior leaflet of the mitral valve is less than the opening angle between the clamp arms 131 since the structure of the opening 122 of the adjustment portion 120 makes the axial movement of the elastic body 123 toward the proximal end no longer restricted, which can reduce pulling of the valve leaflet 1 by the valve clamping device 100, so that the pulling degree of the valve leaflet 1 by the valve clamping device 100 remains within a reasonable range; the elastic body 123 can cushion direct flushing of blood flow inside the valve clamping device 100, prevent the valve clamping device 100 from falling off by the continuous flushing of blood, and also prevent blood from being deposited at a dead angle (C in FIG. 3a) between the clamping portions 130 of the valve clamping device 100 to form thrombus; when the elastic body 123 is under pressure of the valve, a degree of deformation is generated, and the deformation degree increases with the increase of pressure so as to avoid that the squeezing force on the elastic body 123, imposed by the clamp arm 131, in turn acts on the clamp arm 131 after gripping the valve leaflet 1, thereby ensuring that the gripping effect of the valve leaflet 1 by the valve clamping device 100 after release remains consistent with that before release.

Referring to FIG. 15 and FIG. 16, as compared to the valve clamping device 100 of Example 1, a valve clamping device 300 with an adjustable bearing force of Example 2 of the present disclosure differs in that an adjustment portion 320 is in an approximately cone shape in a natural state, the cross-sectional dimension gradually increases from the distal end to the proximal end, a proximal end surface of the adjustment portion 320 forms a bottom surface of the cone, and a connection end between the adjustment portion 320 and the support portion 310 forms an apex of the cone.

The valve clamping device 300 mainly comprises two states, one is an open state, and the other is a closed state. When the clamping portion 330 is closed around the adjustment portion 320, the proximal end of the adjustment portion 320 is on a distal side relative to the proximal end of the clamping portion 330.

In some embodiments, after the clamping portion 330 is radially compressed, a freely hanging end 321b of the adjustment portion 320 is moved toward the proximal end, but the proximal end of the radially compressed adjustment portion 320 is on a distal side relative to the proximal end of the clamping portion 330. In this manner, the adjustment portion 320 is not exposed out of the proximal end surface of the closed clamping portion 330, thereby ensuring that the everted end of the clamping portion 330 abuts the valve leaflet to increase a valve leaflet contact area and conform to the angle and direction of the valve leaflet, and avoiding the risk of thrombus caused by excessive exposure of the adjustment portion 320 to the left atrium.

Referring to FIG. 17 to FIG. 19, in comparison with the valve clamping device 100 of Example 1, an adjustment portion 420 of a valve clamping device 400 with an adjustable bearing force of Example 3 of the present disclosure further comprises a hanging extension 422 at a proximal end thereof, and the extension 422 extends toward a proximal end direction, as shown at B in FIG. 17. For example, the extension 422 may form a circle of surrounding periphery of the adjustment portion 420 and form a boss structure A near the distal connection, and the boss structure A extends perpendicularly to a direction from the distal end to the proximal end.

After the clamping portion 430 is closed around the adjustment portion 420, the extension 422 is exposed and extended from the proximal end of the clamping portion 430 and is not clamped and enclosed by the clamping portion 430. At this time, there is a space between the proximal end of the clamping portion 430 and the extension 422. For example, an axial spacing length between the distal end surface of the extension 422 and the proximal end surface of the clamping portion 430 can be defined as a spacing distance L, and a specific L value may be set by one skilled in the art based on factors such as an anatomical structure. In some embodiments, when the clamping portion 430 is closed around the adjustment portion 420, the extension 422 protrudes from the clamping portion 430, that is, the clamping portion 430 does not clamp the extension 422, which can improve elastic fit between the valve leaflet and the adjustment portion 420.

In some embodiments, when the valve clamping device 400 clamps the valve, the extension 422, which is not clamped and enclosed by the clamping portion 430, may further cooperate with the clamping portion 430 and clamp the valve leaflet. For example, the boss structure A abuts the valve leaflet, increases a clamping force between the valve clamping device 400 and the valve leaflet, thereby improving implantation stability of the valve clamping device 400.

In some embodiments, the proximal end surface of the adjustment portion 420 is recessed toward the distal end. During the clamping process of the clamping portion 430, the recess facilitates radial compression of the adjustment portion 420 and does not cause braided wire accumulation in the vicinity of the extension 422 after compression, and can also reduce a radial reaction force while reducing a compression size, thereby improving safety of the device after compression. On the other hand, the recess also forms an accommodation space of the delivery device, without affecting connection and detachment of the delivery device 200 due to disposition of the extension 422. The extension 422 extends in a direction perpendicular to a direction from the proximal end to the distal end, and the extension 422 is substantially parallel to the direction perpendicular to the direction from the proximal end to the distal end, which can improve the elastic fit between the valve leaflet and the adjustment portion 420.

Figure 1:
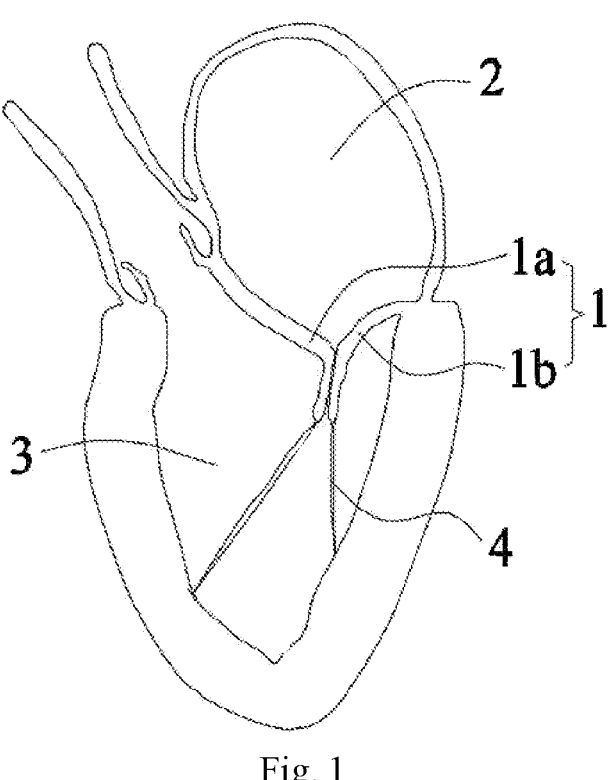
FIG. 1 shows a schematic diagram illustrating a mitral valve in a normal state.
Figure 2:
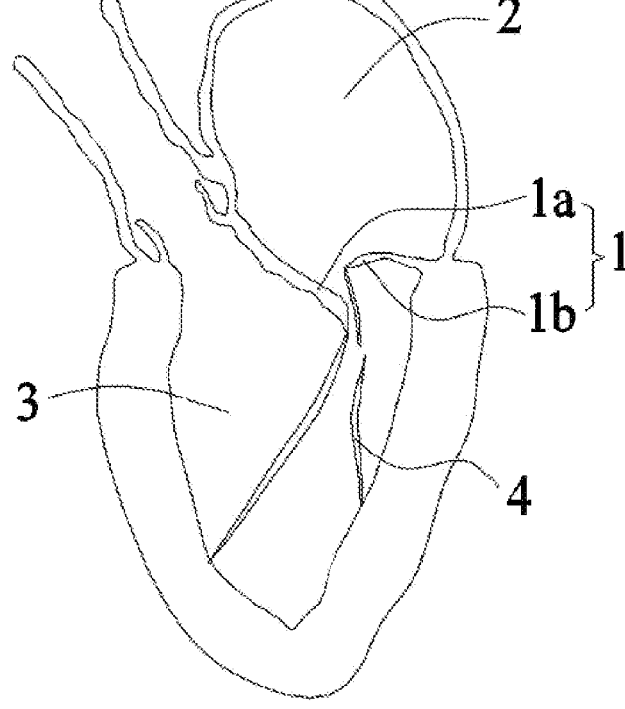
FIG. 2 shows a schematic diagram illustrating a mitral valve with a lesion.

Referring to FIG. 20 and FIG. 2, in comparison with the valve clamping device 400 of Example 3, an adjustment portion 720 of a valve clamping device 700 with an adjustable bearing force of Example 4 of the present disclosure further comprises a hanging extension 722 at a proximal end thereof, and the extension 722 extends outward in a radial direction away from a support portion 710. That is, the extension 722 extends in a direction perpendicular to a direction from the proximal end to the distal end, and the extension 722 is substantially parallel to the direction perpendicular to the direction from the proximal end to the distal end to form an approximate platform structure, and the cross section of the platform structure is in an approximately straight line shape, which can improve elastic fit between the valve leaflet and the adjustment portion 720.

In some embodiments, when the valve clamping device 700 clamps the valve, the extension 722, which is not clamped and enclosed by the clamping portion 730, may further cooperate with the clamping portion 730 and clamp the valve leaflet. For example, the platform structure abuts the valve leaflet, increases a clamping force between the valve clamping device 700 and the valve leaflet, thereby improving implantation stability of the valve clamping device 700.

The proximal end of the adjustment portion 720 is provided with a steel sleeve 723 which facilitates penetration of the delivery device 200. The steel sleeve 723 is disposed on a freely hanging end 721b of the adjustment portion 720. The extension 722 is disposed around the steel sleeve 723, and encloses the steel sleeve 723 when the valve clamping device 700 is compressed radially, which not only prevents the steel sleeve 723 from being in contact with the inner wall of the sheath, but also prevents direct contact of the steel sleeve 723 with body tissues such as the valve leaflet, ensuring delivery safety and implantation safety of the device.

The adjustment portion 720 is externally or internally provided with a biocompatible membrane as a barrier membrane, preventing blood from entering the adjustment portion 720. In a specific application, the adjustment portion 720 may be provided both externally and internally with a biocompatible membrane. In this way, the valve clamping device 700 is more biocompatible, and blood is prevented from entering the inside of the adjustment portion 720 to form thrombus.

Referring to FIG. 22 to FIG. 24, in comparison with the valve clamping device 100 of Example 1, according to a valve clamping device with an adjustable bearing force of Example 5 of the present disclosure, the adjustment portion 520 has a freely hanging end 521b and a distal head 521, the freely hanging end 521b may have an opening 522, the adjustment portion 520 comprises a plurality of first curved surfaces 520A and a plurality of second curved surfaces 520B, the first curved surface 520A and the second curved surface 520B are adjacent to each other and connected together smoothly, that is, the first curved surface 520A is only adjacent to the second curved surface 520B, the second curved surface 520B is also only adjacent to the first curved surface 520A, and the two oppositely disposed first curved surfaces 520A each face one clamp arm, and the area of the second curved surface 520B is smaller than the area of the first curved surface 520A.

In some embodiments, the first curved surface 520A that is relatively larger in area faces the clamp arm, the second curved surface 520B that is relatively smaller in area is smoothly connected between the two first curved surfaces 520A, and as the valve clamping device is closed, the first curved surface 520A of the adjustment portion 520 is squeezed by the clamp arm and the valve leaflet, the adjustment portion 520 extends along the direction of the first curved surface 520A, gradually fit the valve leaflet, thereby better adapting to the shape of the valve leaflet and increasing the contact area between the first curved surface 520A and the valve leaflet, thus reducing the space between the valve clamping device and the valve leaflet, and slowing blood flow and obstructing the blood flow to flush the valve clamping device. In some embodiments, the curvature of the first curved surface 520A can be larger than the curvature of the second curved surface 520B, so that the adjustment portion is in a flat ellipsoidal shape that avoids affecting closing of the clamp arm. In some embodiments, when the clamp arm is closed, the first curved surface 520A of the adjustment portion 520 is compressed by being squeezed by the clamp arm and the valve leaflet, and the adjustment portion 520 extends axially. The first end of the adjustment portion 520 is open and does not hook the distal end of the delivery system, thereby ensuring that the valve clamping device is detached from the delivery device connection site of the valve clamping device in the case of any deformation of the adjustment portion 520.

Referring to FIG. 25 and FIG. 26, in comparison with the valve clamping device of Example 1, the structure of the adjustment portion of the valve clamping device 600 with an adjustable bearing force of Example 6 of the present disclosure is the same as the adjustment portion 120 of Example 1, except for the way that the clamping portion 630 cooperates with the gripping portion 650 to grasp the valve leaflet. In Example 6, the clamping portion 630 comprises a set of clamp arms 631 that can be opened or closed with respect to the support portion 610 and the adjustment portion, the gripping portion 650 comprises a pair of gripping arms 651, and the gripping portion 650 is positioned between the clamping portion 630 and the adjustment portion.

During delivery, the clamping portion 630, the gripping portion 650, and the adjustment portion are housed in the distal end of the delivery device 200, the delivery device 200 is sent into the left ventricle through a transapical route and then crosses the mitral valve orifice to reach the left atrium, the delivery device 200 is withdrawn, so that the adjustment portion and the gripping portion 650 gradually extend out of the delivery device 200 and open within the left atrium; the delivery device 200 continues to be withdrawn until the clamping portion 630 also extends from the delivery device 200 and opens within the left ventricle; then the clamping portion 630 is pushed toward the distal end by the driving portion, the anterior and posterior valve leaflets of the mitral valve are respectively borne on the inner surfaces of the two clamp arms 631 of the clamping portion 630, the gripping portion 650 and the adjustment portion are withdrawn toward the proximal end, that is, the gripping portion 650 is driven to move in the direction of the clamping portion 630, thereby capturing the valve leaflet between the gripping portion 650 and the clamping portion 630, then the clamping portion 630 is driven to close with respect to the adjustment portion and the support portion 610, thereby fixing the anterior leaflet and the posterior leaflet respectively between one clamp arm 631 and one gripping arm 651 disposed correspondingly to the clamp arm 631, then the delivery device 200 is pushed toward the distal end until the valve clamping device 600 is gradually folded and closed; the valve clamping device is disconnected from the delivery device 200, thereby implanting the valve clamping device on the mitral valve and drawing the anterior leaflet and the posterior leaflet of the mitral valve toward each other to form a double orifice structure.

The valve clamping system of the present disclosure comprises any one of the valve clamping devices described above and a delivery device capable of delivering the valve clamping device from outside the body to the vicinity of the mitral valve and clamping the valve leaflet. The above description of the valve clamping device is for purpose of example only and is not limitation of the present disclosure, and a valve clamping device and a valve clamping system comprising the valve clamping device obtained by one skilled in the art based upon the teachings of the present disclosure are within the scope of the present disclosure.

It should be noted that in this disclosure, relational terms such as "first", "second" and the like are only used to distinguish one entity or operation from another entity or operation, and do not necessarily require or imply that there is any such actual relationship or sequence among entities or operations. Moreover, the terms "comprise", "include" or any other variants thereof are intended to cover non-exclusive inclusion, so that a process, method, article, or device that comprises a series of elements comprises not only those elements, but those other elements that are not explicitly listed, or also comprises elements inherent to this process, method, article or equipment. If there are no more restrictions, the element defined by the sentence "comprising a . . . " does not exclude the existence of other same elements in the process, method, article, or equipment that comprises the element.

The above are only specific embodiments of the present disclosure to enable one skilled in the art to understand or implement the disclosure. Various modifications to these examples will be obvious to one skilled in the art, and the general principles defined herein can be implemented in other examples without departing from the spirit or scope of the present disclosure. Therefore, the present disclosure will not be limited to the examples shown in the present disclosure, but should conform to the widest scope consistent with the principles and novel features of the present disclosure.

What is claimed is:

1. A valve clamping device with an adjustable bearing force, comprising:
   a support portion comprising a connecting end and a free end disposed oppositely;
   a hollow adjustment portion made of a shape memory material, wherein one end of the adjustment portion is sleeved outside the connecting end and connected to the support portion, and another end of the adjustment portion hangs in air;
   a clamping portion enclosed outside the adjustment portion; and
   a driving portion connected to the clamping portion to drive the clamping portion to open or close around the adjustment portion;
   wherein the free end of the support portion is located within the adjustment portion, and a proximal end of the adjustment portion is spaced apart from a proximal end of the support portion.

2. The valve clamping device with an adjustable bearing force of claim 1, wherein the adjustment portion is in an approximately cone shape in a natural state, a proximal end surface of the adjustment portion forms a bottom surface of a cone, and a connection end between the adjustment portion and the support portion forms an apex of the cone.

3. The valve clamping device with an adjustable bearing force of claim 1, wherein the adjustment portion comprises a hanging extension, and the extension extends toward a proximal end direction and forms a circle of surrounding periphery of the adjustment portion.

4. The valve clamping device with an adjustable bearing force of claim 1, wherein the adjustment portion comprises a hanging extension, and the extension extends in a radial direction away from the support portion and forms a circle of surrounding periphery of the adjustment portion.

5. The valve clamping device with an adjustable bearing force of claim 1, wherein the adjustment portion comprises a plurality of first curved surfaces and a plurality of second curved surfaces, the first curved surface and the second curved surface are adjacent to each other, two oppositely disposed first curved surfaces of the plurality of first curved surface face the clamping portion respectively, and an area of the first curved surface is larger than an area of the second curved surface.

6. The valve clamping device with an adjustable bearing force of claim 1, wherein a biocompatible membrane or a biocompatible coating is provided outside and/or inside the adjustment portion.

7. The valve clamping device with an adjustable bearing force of claim 1, wherein the adjustment portion comprises an elastic body having a natural state and a compressed state, an end of the elastic body is connected to the support portion, another end of the elastic body has an opening, and a size of the opening is smaller than or equal to a size of the free end of the support portion when the elastic body is in the compressed state.

8. The valve clamping device with an adjustable bearing force of claim 7, wherein a proximal end edge of the elastic body is enclosed to form the opening.

9. The valve clamping device with an adjustable bearing force of claim 7, wherein a proximal end of the elastic body is folded and then provided with a head.

10. The valve clamping device with an adjustable bearing force of claim 1 wherein the clamping portion comprises at least two clamp arms symmetrically disposed with respect to the adjustment portion, and the driving portion is connected to each of the clamp arms to drive each of the clamp arms to rotate about the adjustment portion.

11. The valve clamping device with an adjustable bearing force of claim 10, further comprising a gripping portion that is disposed between the clamping portion and the adjustment portion, can be opened or closed with respect to the adjustment portion, and is at least partially located on an inner surface of the clamping portion when both the gripping portion and the clamping portion are opened.

12. The valve clamping device with an adjustable bearing force of claim 11, wherein a biocompatible membrane is applied to an outside of both the clamp arm and the gripping portion.

13. The valve clamping device with an adjustable bearing force of claim 1, further comprising a base fixedly connected to the support portion, wherein the clamping portion is rotatably connected to the base.

14. The valve clamping device with an adjustable bearing force of claim 13, wherein the driving portion comprises: a drive shaft; a connection seat; and at least two connecting rods, wherein one end of each of the connecting rods is connected to the clamping portion and another end is pivotally connected to the connection seat; one end of the drive shaft is connected to the connection seat and another end movably penetrates the base.

15. The valve clamping device with an adjustable bearing force of claim 14, further comprising a locking portion disposed in the base, which limits relative movement of the drive shaft and the base.

16. A valve clamping system, comprising the valve clamping device with an adjustable bearing force of claim 1 and a delivery device, wherein the delivery device comprises: a pushing shaft having an axial length and a mandrel movably penetrating the pushing shaft, wherein the pushing shaft and the support portion are detachably connected, and the mandrel is connected to the driving portion to drive the clamping portion to open and close with respect to the support portion.

17. The valve clamping device with an adjustable bearing force of claim 1, wherein the free end of the support portion is permanently located within the adjustment portion.

\* \* \* \* \*